United States Patent
Homan (10) Patent No.: US 8,740,772 B2
(45) Date of Patent: Jun. 3, 2014

(54) POSITION INFORMATION ESTIMATION SYSTEM

(71) Applicant: Olympus Medical Systems Corp., Tokyo (JP)

(72) Inventor: Masatoshi Homan, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/630,704

(22) Filed: Sep. 28, 2012

(65) Prior Publication Data

US 2013/0123575 A1  May 16, 2013

Related U.S. Application Data

(63) Continuation of application No. PCT/JP2012/051465, filed on Jan. 24, 2012.

(30) Foreign Application Priority Data

Feb. 23, 2011 (JP) ................................. 2011-037457

(51) Int. Cl.
*A61B 1/00* (2006.01)
*A61B 1/04* (2006.01)

(52) U.S. Cl.
CPC .............. *A61B 1/041* (2013.01); *A61B 1/00016* (2013.01); *A61B 1/00006* (2013.01)
USPC ........... 600/103; 600/101; 600/424; 600/117; 600/118

(58) Field of Classification Search
CPC ................ A61B 1/041–1/042; A61B 1/00016; A61B 5/06
USPC ......................................... 600/101, 103, 424
See application file for complete search history.

(56) References Cited

U.S. PATENT DOCUMENTS

2005/0148816 A1* 7/2005 Glukhovsky et al. ......... 600/103
2006/0036166 A1   2/2006 Horn
(Continued)

FOREIGN PATENT DOCUMENTS

JP   2005-304511 A   11/2005
JP     2006-296 A    1/2006
(Continued)

OTHER PUBLICATIONS

International Search Report PCT/JP2012/051465 dated Mar. 6, 2012.

(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

A position information estimation system includes: a body-insertable apparatus that is inserted into a subject and moves through an inside of the subject; a receiving unit that receives information from the body-insertable apparatus; and an information processor that performs processes on the information acquired from the receiving unit. The receiving unit includes an acquisition antenna that includes a plurality of receiving antennas and acquires information from the body-insertable apparatus. The information processor includes: a calculation unit that calculates difference values between signal levels acquired from the plurality of receiving antennas and corresponding signal levels acquired from the plurality of receiving antennas; a determination unit that compares each of the difference values with a threshold and determining whether to estimate position information; and a position information estimation unit that estimates position information of the body-insertable apparatus when the determination unit has determined that it is necessary to estimate the position information.

7 Claims, 9 Drawing Sheets

(56) References Cited

U.S. PATENT DOCUMENTS

| | | | |
|---|---|---|---|
| 2006/0120484 A1* | 6/2006 | Matsumoto et al. | 375/316 |
| 2007/0167743 A1 | 7/2007 | Honda et al. | |
| 2007/0252892 A1* | 11/2007 | Fujita et al. | 348/65 |
| 2008/0033257 A1* | 2/2008 | Yokoi et al. | 600/300 |
| 2008/0154124 A1* | 6/2008 | Iustin et al. | 600/424 |
| 2008/0297291 A1* | 12/2008 | Kawano et al. | 335/285 |
| 2009/0043164 A1* | 2/2009 | Hasegawa et al. | 600/118 |
| 2009/0093678 A1* | 4/2009 | Kimura et al. | 600/117 |
| 2010/0179782 A1* | 7/2010 | Kimura et al. | 702/94 |
| 2010/0204566 A1* | 8/2010 | Uchiyama et al. | 600/424 |
| 2010/0305426 A1* | 12/2010 | Kimura et al. | 600/411 |
| 2011/0181273 A1* | 7/2011 | Iida et al. | 324/207.11 |
| 2011/0184690 A1* | 7/2011 | Iida et al. | 702/150 |
| 2011/0208019 A1* | 8/2011 | Sato et al. | 600/302 |
| 2011/0224490 A1* | 9/2011 | Kimura et al. | 600/118 |
| 2011/0255757 A1* | 10/2011 | Nishimura et al. | 382/128 |
| 2011/0255758 A1* | 10/2011 | Nishimura et al. | 382/128 |
| 2011/0255759 A1* | 10/2011 | Nishimura et al. | 382/128 |
| 2011/0273548 A1* | 11/2011 | Uchiyama et al. | 348/68 |
| 2012/0143047 A1* | 6/2012 | Kimura et al. | 600/424 |

FOREIGN PATENT DOCUMENTS

| | | |
|---|---|---|
| JP | 2006-26163 A | 2/2006 |
| JP | 2006-68501 A | 3/2006 |
| WO | WO 2007/123217 A1 | 11/2007 |
| WO | WO 2009/041524 A1 | 4/2009 |
| WO | WO 2010/044389 A1 | 4/2010 |

OTHER PUBLICATIONS

Extended Supplementary European Search Report dated Jul. 30, 2013 in European Patent Application No. 12749273.4.

* cited by examiner

POSITION INFORMATION ESTIMATION SYSTEM

CROSS-REFERENCE TO RELATED APPLICATION

This application is a continuation of PCT international application Ser. No. PCT/JP2012/051465 filed on Jan. 24, 2012 which designates the United States, incorporated herein by reference, and which claims the benefit of priority from Japanese Patent Applications No. 2011-037457, filed on Feb. 23, 2011, incorporated herein by reference.

BACKGROUND OF THE INVENTION

1. Field of the Invention

The present invention relates to, for example, a position information estimation system that estimates position information of a capsule endoscope inserted into a subject.

2. Description of the Related Art

Conventionally, endoscopes have been in widespread use as medical observation apparatuses that are inserted into subjects to enable in-vivo observation. In recent years, endoscopes (capsule endoscopes) to be swallowed have been developed also, each equipped with devices, such as an imaging device and a communication device that wirelessly transmits image data captured by this imaging device, inside a capsule-shaped casing. A capsule endoscope has the function of, after being swallowed through the mouth of a subject for in-vivo observation, sequentially imaging internal organs such as an esophagus, a stomach, and a small intestine while moving inside these organs along with the peristaltic movement of these organs, until the natural egestion of the endoscope from the subject.

While the capsule endoscope moves in a body cavity, image data captured by the capsule endoscope in the body cavity are sequentially transmitted to the outside of the body by radio communication. Then, these image data are accumulated in a memory provided inside or outside of a receiving device outside of the body, or are displayed as images on a display provided to the receiving device. A doctor or a nurse is enabled to make diagnoses based on images that have been obtained by importing the image data, accumulated in the memory, to an information processor through a cradle having the receiving device inserted therein, and are displayed on a display of this information processor, or alternatively, images that have been received by the receiving device and are displayed on the display thereof.

Incidentally, for receiving a radio signal from a capsule endoscope, a receiving device in general has two or more antennas placed outside of a subject in a dispersed manner, and is configured to select one of the antennas that shows the highest signal level in the reception, and receive the radio signal via the thus selected antenna. One known example of thus configured receiving devices is a receiving device that switches reception between two or more receiving antennas placed outside of a subject and estimates the position of a capsule endoscope, which is the source of a radio signal, based on the strengths of electric field received by the respective receiving antennas.

Examples of a position information system that estimates the position of the above described capsule endoscope includes a moving state detection system disclosed by Japanese Unexamined Patent Publication No. 2006-26163. The moving state detection system detects a moving state of a capsule endoscope that moves inside a subject and outputs a sensor signal that attenuates in accordance with the propagation distance thereof. This moving state detection system includes a moving state derivation unit that, after a receiving antenna has received a sensor signal, derives the moving state based on the signal level in the reception.

Further, this moving state detection system includes a determination unit that determines the moving state of the capsule endoscope based on the selection as to which one of receiving antennas to use for receiving a sensor signal. The determination unit determines whether the capsule endoscope is currently in a low-speed moving state or in a high-speed moving state. This determination unit enables efficient diagnoses that only require, in checking images captured by the capsule endoscope, checking of some images in a group of images that corresponds to the capsule endoscope determined to be in the low-speed moving state.

SUMMARY OF THE INVENTION

According to one aspect of the present invention, there is provided a position information estimation system comprising: a body-insertable apparatus that is inserted into a subject and moves through an inside of the subject; a receiving unit that receives information from the body-insertable apparatus; and an information processor that performs processes on the information acquired from the receiving unit, wherein the receiving unit includes an acquisition antenna that includes a plurality of receiving antennas and acquires the information from the body-insertable apparatus, and the receiving unit or the information processor includes: a calculation unit that calculates difference values between signal levels acquired from the plurality of receiving antennas and corresponding signal levels previously acquired from the plurality of receiving antennas; a determination unit that compares each of the difference values and a threshold and determines whether to estimate position information; and a position information estimation unit that, when the determination unit has determined that it is necessary to estimate the position information, estimates position information of the body-insertable apparatus.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

The best modes to carry out the present invention are described below in detail in connection with the drawings. Note that the following embodiments are not intended to limit the present invention. Additionally, in connection with the following description, the drawings illustrate shapes, sizes, and positional relationships merely in such a manner as to make the substance of the present invention understandable. Therefore, the present invention is not limited only to the shapes, the sizes, and the positional relationships illustrated as examples in the drawings.

First Embodiment

Figure 1:
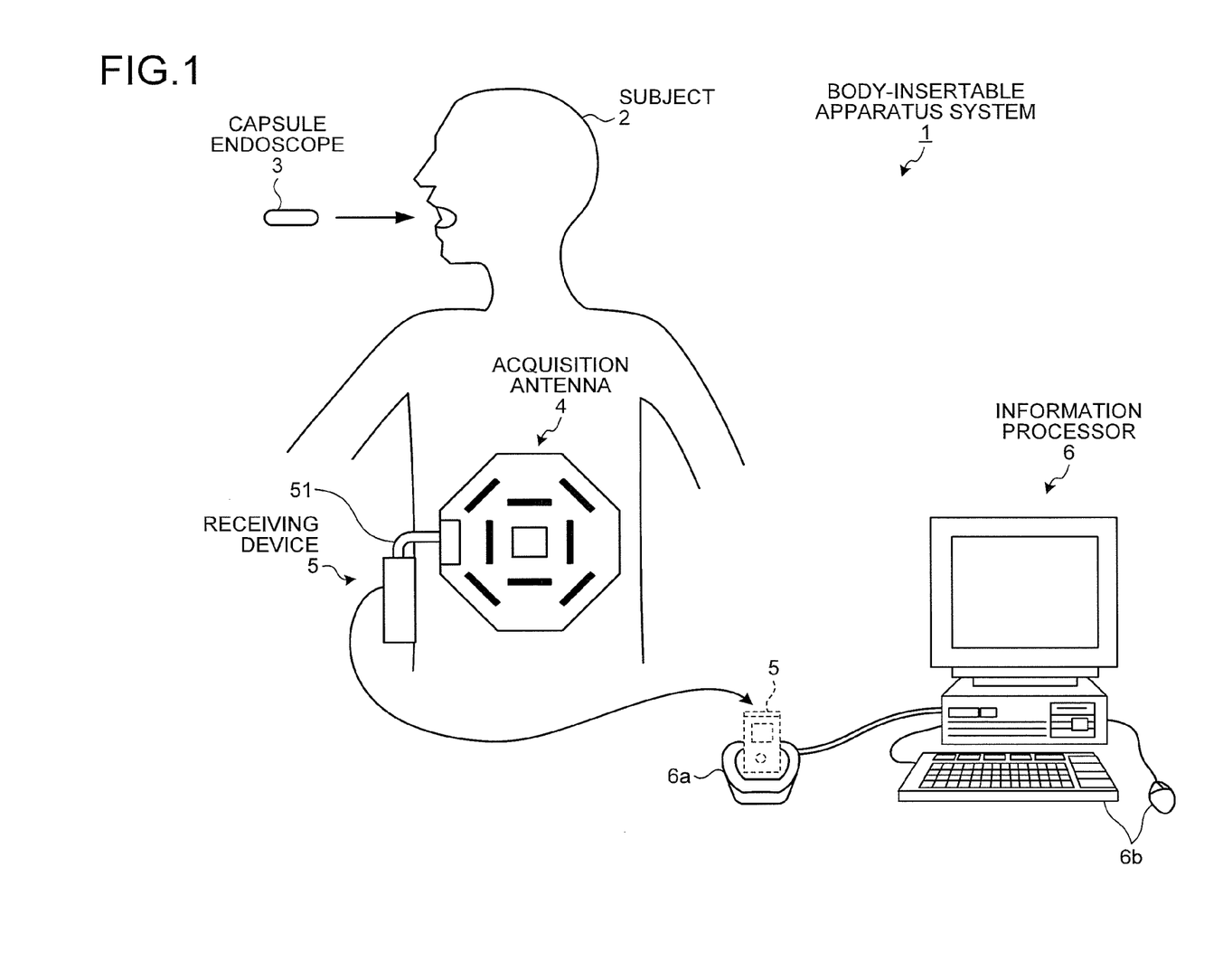
FIG. 1 is a schematic diagram illustrating the entire configuration of a body-insertable apparatus system according to a first embodiment of the present invention.
Figure 2:
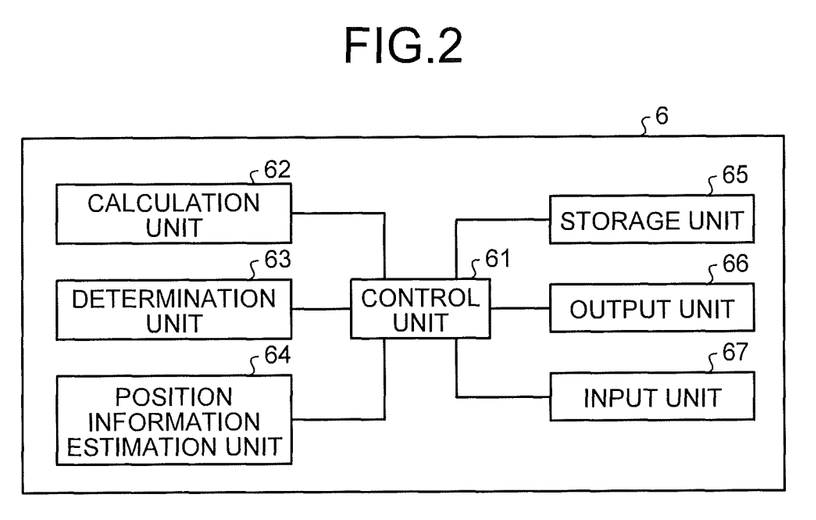
FIG. 2 is a block diagram illustrating the configuration of an information processor of the body-insertable apparatus system according to the first embodiment of the present invention.

Firstly, a position information estimation system according to a first embodiment of the present invention is described in detail with reference to the drawings. FIG. 1 is a schematic diagram illustrating the entire configuration of a body-insertable apparatus system according to the first embodiment of the present invention. In addition, FIG. 2 is a block diagram illustrating the configuration of an information processor of the body-insertable apparatus system according to the first embodiment of the present invention.

As illustrated in FIG. 1, a body-insertable apparatus system 1 includes: a capsule endoscope 3 provided as a body-insertable apparatus that captures in-vivo images of the inside of a subject 2; an acquisition antenna 4 that receives a radio signal transmitted from the capsule endoscope 3 inserted into the inside of the subject 2; a receiving device 5 that performs predetermined processes on radio signals inputted from the acquisition antenna 4 and then stores the radio signals; and an information processor 6 that processes or displays, or processes and displays, images corresponding to image data of the inside of the subject 2 that have been captured by the capsule endoscope 3. The acquisition antenna 4 and the receiving device 5 constitute a receiving unit.

The capsule endoscope 3 has an image capturing function with which to capture images of the inside of the subject 2, and a radio communication function with which to transmit, to the receiving device 5, image data obtained by capturing images of the inside of the subject 2. Further, an antenna 31 (see FIG. 6) formed of a circular coil or a circular loop is placed inside the capsule endoscope 3. The capsule endoscope 3 is swallowed by the subject 2, thereby passing through the esophagus in the inside of the subject 2 and moving through the inside of the body cavity along with the peristaltic movement of the lumen of the alimentary canal. The capsule endoscope 3 sequentially captures images of the inside of the body cavity of the subject 2 at minute time intervals, for example, of 0.5 seconds while moving through the inside of the body cavity. In this case, the capsule endoscope 3 generates transmitter signals each containing image data and received-electric-field strength detection data. The received-electric-field strength detection data contains position information (a beacon) that facilitates detection of the strength of an electric field to be received. Then, the capsule endoscope 3 transmits to the receiving device 5 radio signals obtained by modulating the thus generated transmitter signals.

The acquisition antenna 4 periodically receives a radio signal from the capsule endoscope 3, and outputs a radio signal to the receiving device 5 via an antenna cable 51. Note that the acquisition antenna 4 is attached to the subject 2 by being fixed thereto by use of a belt or the like when an examination is performed thereon.

The receiving device 5 acquires image data of the inside of the subject 2 based on radio signals wirelessly transmitted from the capsule endoscope 3 via the acquisition antenna 4. The receiving device 5 stores, in a memory, position information and time information, which indicates times, while associating the position information and time information with the received image data. The receiving device 5 is carried by the subject 2 while the capsule endoscope 3 is capturing images, that is, during a period between when the capsule endoscope 3 is swallowed through the mouth of the subject 2 and when the capsule endoscope 3 is egested from the subject 2 after passing through the alimentary canal. After the completion of the examination using the capsule endoscope 3, the receiving device 5 is removed from the subject 2 and connected to the information processor 6 in order to transfer information, such as image data, received from the capsule endoscope 3.

The information processor 6 is formed by use of a workstation or personal computer that is provided with a display unit such as a liquid crystal display. The information processor 6 displays images corresponding to image data of the inside of the subject 2 that have been acquired via the receiving device 5. To the information processor 6, a cradle 6a that reads out image data from the memory of the receiving device 5, and an operation input device 6b such as a keyboard or a mouse are connected.

Further, as illustrated in FIG. 2, the information processor 6 includes: a control unit 61 that controls the entirety of the information processor 6; a calculation unit 62 that calculates difference values for the signal levels received by the acquisition antenna 4; a determination unit 63 that determines, based on the difference values, the necessity to perform a position information estimation process; a position information estimation unit 64 that estimates position information of the capsule endoscope 3 when the determination unit 63 has determined that it is necessary to perform the position information estimation process; a storage unit 65 that stores image data and signal levels that are received from the capsule endoscope 3; an output unit 66 formed by use of a display, a printer, a speakerphone or the like; and an input unit 67 that acquires information from devices such as the operation input device 6b formed of a keyboard, a mouse or the like. Note that the storage unit 65 is formed by use of a hard disk, which magnetically stores information, and a memory in which various programs, according to this embodiment, to be used in processes when the body-insertable apparatus system 1 performs the processes are electrically stored after being loaded from a hard disk.

The position information estimation unit 64 acquires the highest signal level out of the signal levels of different receiving antennas included in the acquisition antenna 4, and estimates the position of the capsule endoscope 3 by deriving the position information (the position and the direction of the antenna) of the capsule endoscope 3 (the position information estimation process).

The cradle 6a acquires image data and relevant data from the memory of the receiving device 5 with the receiving device 5 attached thereto, and transfers the acquired various data to the information processor 6. The relevant data includes signal-level information of received signals, time information, and identification information of the capsule endoscope 3 that have been associated with the image data.

The operation input device 6b accepts input from a user. While operating the operation input device 6b, the user views images of the inside of the subject 2 that are sequentially displayed by the information processor 6. The user thereby observes biological sections, such as the esophagus, the stomach or the large intestine, of the subject 2 to diagnose the subject 2.

Figure 3:
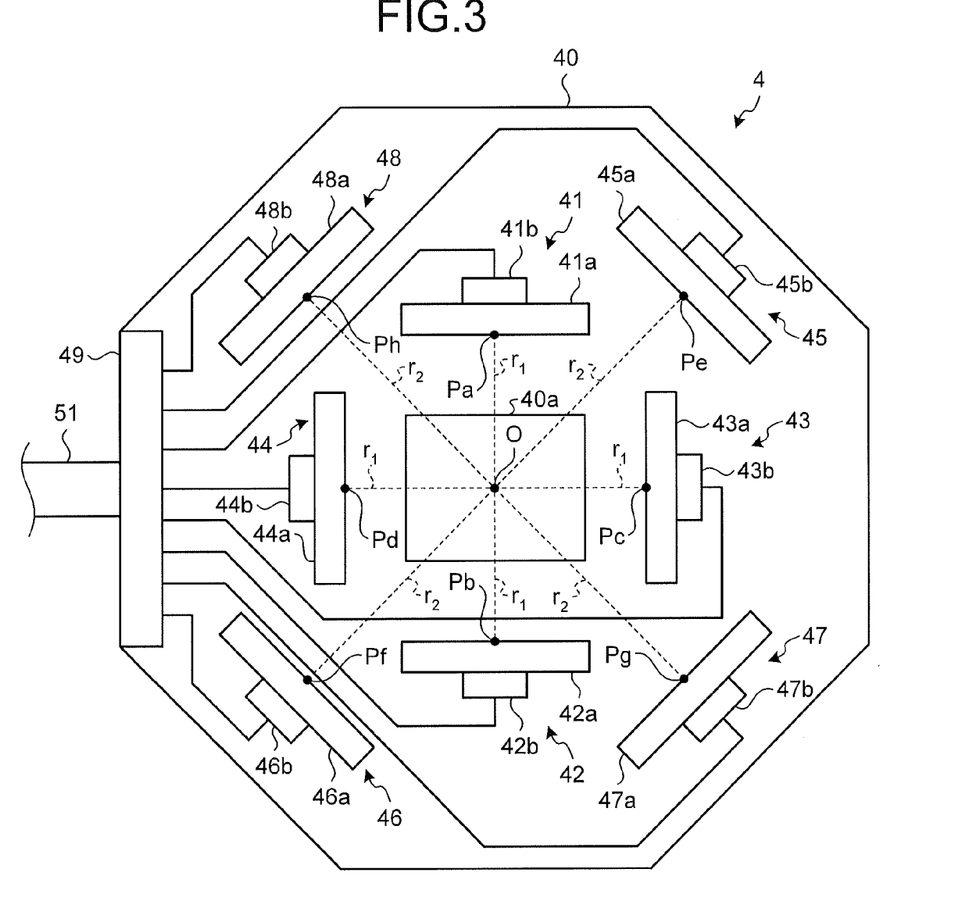
FIG. 3 is a schematic diagram illustrating the configuration of an acquisition antenna in the body-insertable apparatus system according to the first embodiment of the present invention.

Next, the detailed configuration of the acquisition antenna 4 illustrated in FIG. 3 is described. FIG. 3 is a schematic diagram illustrating the configuration of the acquisition antenna of the body-insertable apparatus system according to the first embodiment of the present invention. The acquisition antenna 4 includes a plate section 40, a first receiving antenna 41, a second receiving antenna 42, a third receiving antenna 43, a fourth receiving antenna 44, a fifth receiving antenna 45, a sixth receiving antenna 46, a seventh receiving antenna 47, an eighth receiving antenna 48, and a connector section 49, as illustrated in FIG. 3. The respective first to eighth receiving antennas 41 to 48 are connected to the connector section 49 and provided on the singly provided plate section 40.

The plate section 40 is formed by use of a flexible substrate. The principal plane of the plate section 40 forms a substantially octagonal shape. The plate section 40 is formed into a size that is sufficient to cover the entirety of the abdominal region of the subject 2. The plate section 40 has an opening section 40a. The opening section 40a is formed in such a manner that the center thereof corresponds to a reference point O of the plate section 40. The opening section 40a functions as an alignment section with reference to which the position of the subject 2 is determined when the plate section 40 is attached to the subject 2. This enables the acquisition antenna 4 to facilitate alignment in the attachment of the plate section 40 to the subject 2. Note that a transparent member, such as a plastic sheet, may be provided to the opening section 40a. Further, the principal plate of the plate section 40 does not need to be substantially octagonal, and may be rectangular or the like.

The first receiving antenna 41 and the second receiving antenna 42 are placed at positions opposed to each other across the reference point O. The first receiving antenna 41 and the second receiving antenna 42 are placed at positions the same distance away from the reference point O. Specifically, the first receiving antenna 41 and the second receiving antenna 42 are placed at positions on the plate section 40 that allow points Pa and Pb therein, the distances from which to the reference point O is the shortest distance to the reference point O from the first receiving antenna 41 and the second receiving antenna 42, to both be located a distance of $r_1$ away from the reference point O. The first receiving antenna 41 and the second receiving antenna 42 have an element section 41a and an element section 42a, respectively, formed of printed wiring on the plate section 40. The first receiving antenna 41 and the second receiving antenna 42 have active circuits 41b and 42b, which are connected to the respective element sections 41a and 42a. The respective active circuits 41b and 42b are formed of plane circuits on the plate section 40. The active circuits 41b and 42b perform impedance matching, an amplification process including amplification and attenuation of a received radio signal, a transformation process for balance-to-unbalance transformation, and the like for the first receiving antenna 41 and the second receiving antenna 42, respectively. The first receiving antenna 41 and the second receiving antenna 42 are individually connected via planar transmission lines (strip lines) to the connector section 49 provided on the plate section 40.

The third receiving antenna 43 and the fourth receiving antenna 44 are placed at positions located 90 degrees around the reference point O from the first receiving antenna 41 and the second receiving antenna 42, respectively, on the same plane as the first receiving antenna 41 and the second receiving antenna 42 are located. The third receiving antenna 43 and the fourth receiving antenna 44 are placed at positions on the plate section 40 that allow points Pc and Pd therein to both be located a distance of $r_1$ away from the reference point O. The third receiving antenna 43 and the fourth receiving antenna 44 have an element section 43a and an element section 44a, respectively, formed of printed wiring on the plate section 40. The third receiving antenna 43 and the fourth receiving antenna 44 have active circuits 43b and 44b, which are connected to the respective element sections 43a and 44a. The third receiving antenna 43 and the fourth receiving antenna 44 are individually connected via planar transmission lines (strip lines) to the connector section 49.

The fifth receiving antenna 45 and the sixth receiving antenna 46 are placed at positions that are, on the same plane as above, located 45 degrees around the reference point O from the first receiving antenna 41 and the second receiving antenna 42, respectively. The fifth receiving antenna 45 and the sixth receiving antenna 46 are placed at positions that are, on the same plane as above, closer to the outer circumference than the first receiving antenna 41 and the second receiving antenna 42 are. Specifically, the fifth receiving antenna 45 and the sixth receiving antenna 46 are placed at positions on the plate section 40 that allow points Pe and Pf therein to both be located a distance of $r_2$ ($r_1 < r_2$) away from the reference point O. The fifth receiving antenna 45 and the sixth receiving antenna 46 have an element section 45a and an element section 46a, respectively, formed of printed wiring on the plate section 40. The fifth receiving antenna 45 and the sixth receiving antenna 46 have active circuits 45b and 46b, which are connected to the respective element sections 45a and 46a. The fifth receiving antenna 45 and the sixth receiving antenna 46 are individually connected to the connector section 49 via planar transmission lines.

The seventh receiving antenna 47 and the eighth receiving antenna 48 are placed at positions that are, on the same plane as above, located 90 degrees around the reference point O from the fifth receiving antenna 45 and the sixth receiving antenna 46. The seventh receiving antenna 47 and the eighth receiving antenna 48 are placed at positions that are, on the same plane as above, closer to the outer circumference than the first receiving antenna 41 and the second receiving antenna 42 are. Specifically, the seventh receiving antenna 47 and the eighth receiving antenna 48 are placed at positions on the plate section 40 that allow points Pg and Ph thereon to both be located a distance of $r_2$ away from the reference point O. The seventh receiving antenna 47 and the eighth receiving antenna 48 have an element section 47a and an element section 48a, respectively, formed of printed wiring on the plate section 40. The seventh receiving antenna 47 and the eighth receiving antenna 48 have active circuits 47b and 48b, which are connected to the respective element sections 47a and 48a. The seventh receiving antenna 47 and the eighth receiving antenna 48 are individually connected to the connector section 49 via planar transmission lines.

Figure 4:
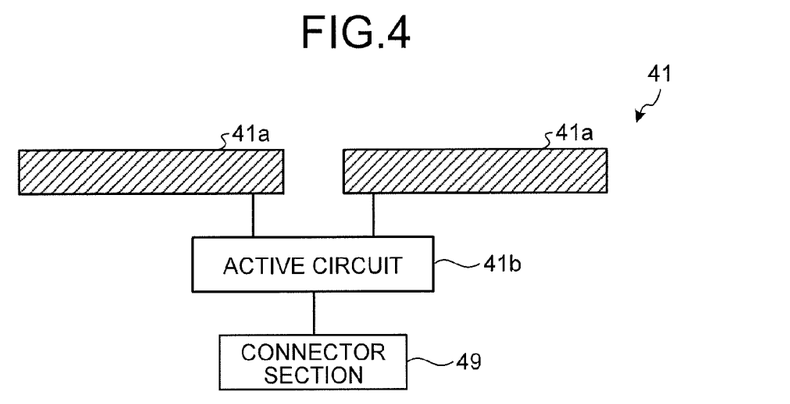
FIG. 4 is a schematic diagram illustrating the configuration of the main portion of the acquisition antenna in the body-insertable apparatus system according to the first embodiment of the present invention.

Here, the configuration of the first receiving antenna 41 described above with reference to FIG. 3 is described in detail. FIG. 4 is a block diagram illustrating the configuration of the main portion of the first receiving antenna 41.

As illustrated in FIG. 4, the first receiving antenna 41 is formed by use of a balancing antenna. Specifically, the first receiving antenna 41 is formed by use of a dipole antenna in which the element section 41a has two linear conductors formed bilaterally symmetrically, on straight lines, and into the same size. This makes a loss in cross-polarization larger than a loss in co-polarization in the first receiving antenna 41. Note that each of the above described second to eighth receiving antennas 42 to 48 has the same configuration as the first receiving antenna 41, and description thereof is therefore omitted. Further, in this first embodiment, the number of receiving antennas is not needed to be understood as being limited to 8, and may be more than 8.

The above described configurations enables the acquisition antenna 4 to, regardless of the direction and the position of the capsule endoscope 3 inside the subject 2, receive waves of any polarization that are transmitted by the capsule endoscope 3. Note that the placement of the first to eighth receiving antennas 41 to 48 is not limited to the illustration in FIG. 3, and, for example, a distance of $r_1$ from the reference point O may be set equal to a distance of $r_2$. Further, the acquisition antenna does not need to be fixedly placed on one sheet, and the respective receiving antennas may be separately secured to the subject 2.

Figure 5:
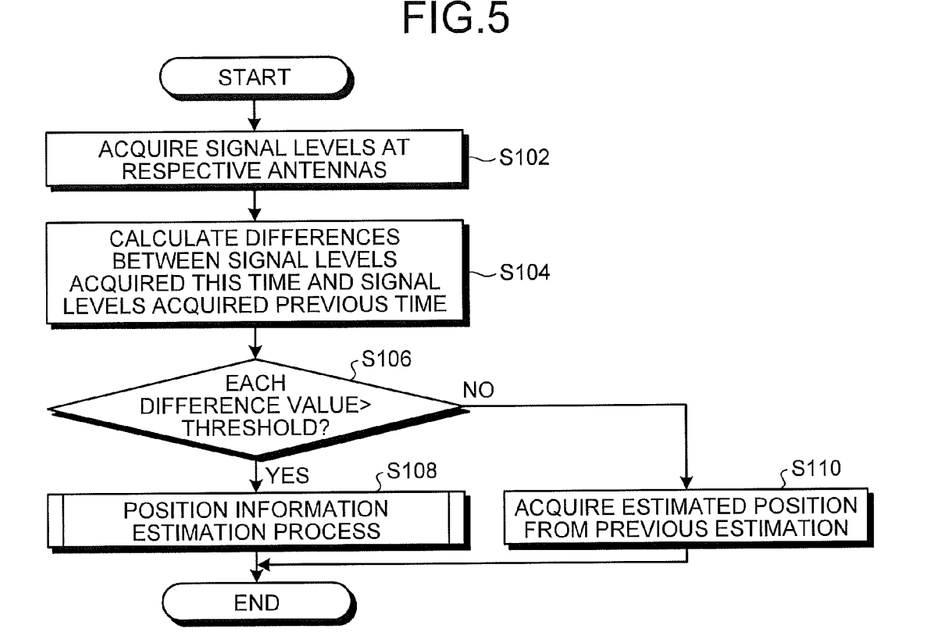
FIG. 5 is a flowchart illustrating a determination process, in the body-insertable apparatus system according to the first embodiment of the present invention, as to the necessity to perform position estimation.

Next, a process for determining the necessity for the above described position information estimation unit 64 to perform the position information estimation process is described with reference to FIG. 5. FIG. 5 is a flowchart illustrating the determination process, in the body-insertable apparatus system according to this first embodiment, as to the necessity to perform the position estimation. First of all, the control unit 61 acquires signal levels acquired by the respective first to eighth receiving antennas 41 to 48 (step S102).

Thereafter, the calculation unit 62 calculates the absolute values (difference values) of differences between signal levels acquired at the first to eighth receiving antennas 41 to 48 the previous time and corresponding signal levels acquired this time at the first to eighth receiving antennas 41 to 48 (step S104). Note that, when signal levels acquired this time are those obtained for the first time since the start of an examination, the signal levels acquired the previous time are set to zero in calculation of the difference values.

The determination unit 63 compares each of the thus calculated difference values with a predetermined threshold (step S106). Here, when the determination unit 63 has determined that at least any one of the difference values is larger than the predetermined threshold (step S106: Yes), the control unit 61 performs the later described position information estimation process (step S108).

On the other hand, when the determination unit 63 has determined that all of the difference values are smaller than or equal to the predetermined threshold (step S106: No), the control unit 61 refers to the storage unit 65 to acquire an estimated position estimated the previous time, and associates this estimated position with image data on which to perform the determination process. When the difference values are smaller than or equal to the predetermined threshold, it is allowed to determine that the capsule endoscope 3 has not been moved so much as to require position estimation thereof to be performed again. Therefore, the control unit 61 acquires the estimated position from the previous time (step S110).

Figure 6:
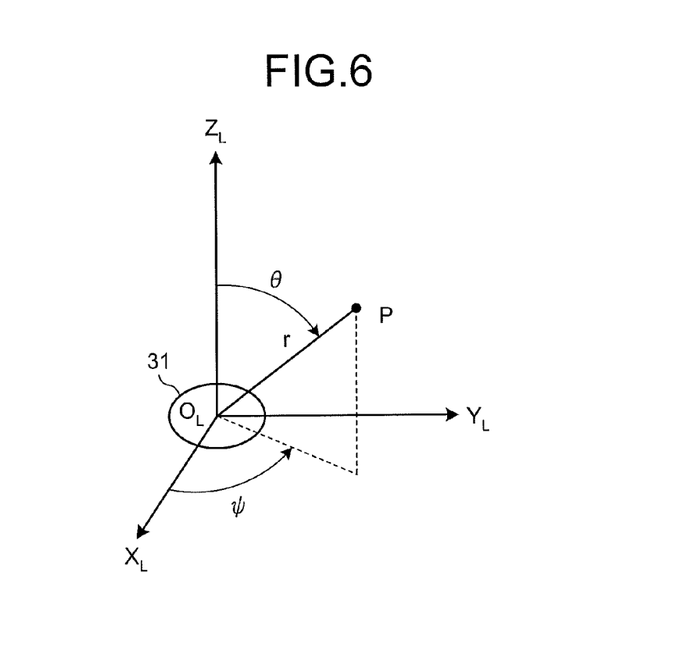
FIG. 6 is a diagram illustrating an orthogonal coordinate system with the origin set at an antenna of a capsule endoscope of the body-insertable apparatus system according to the first embodiment of the present invention.
Figure 7:
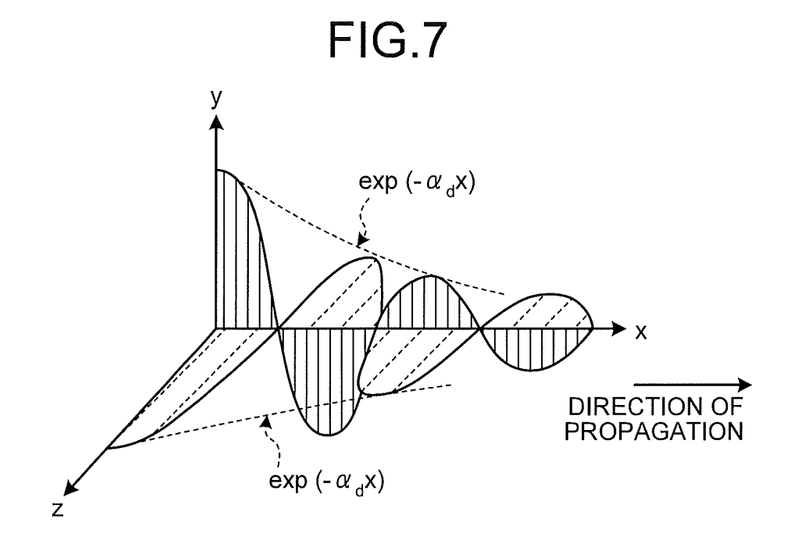
FIG. 7 is a diagram illustrating how an electromagnetic wave attenuates while being propagated through a medium.
Figure 8:
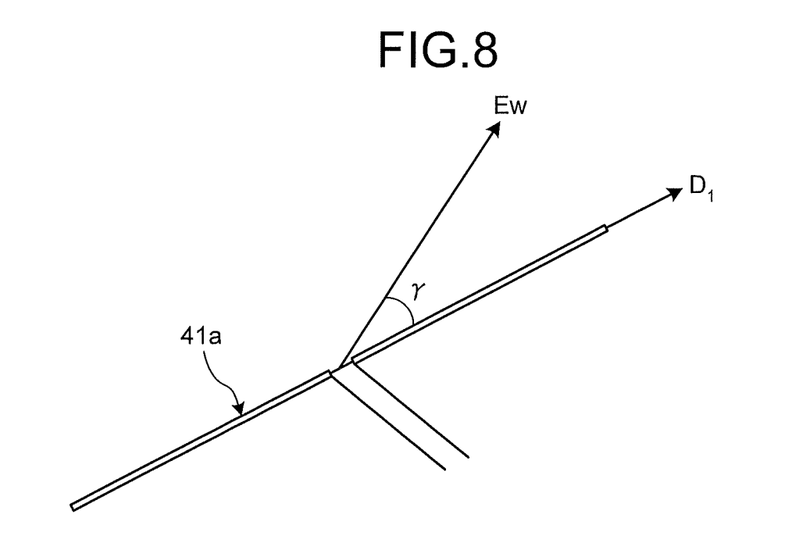
FIG. 8 is a diagram illustrating an electromotive force detected when a magnetic field generated by the antenna illustrated in FIG. 6 is received by an antenna attached to a body surface.

Next, the position information estimation process for estimating the position and the direction of the capsule endoscope 3 from signals indicating received signal levels, which are detected using the first to eighth receiving antennas 41 to 48 of the acquisition antenna 4 is described with reference to FIGS. 6 to 9. FIG. 6 is a diagram illustrating an orthogonal coordinate system with the origin set at the antenna of the capsule endoscope of the body-insertable apparatus system according to the first embodiment of the present invention. FIG. 7 is a diagram illustrating how an electromagnetic wave attenuates while being propagated through a medium. FIG. 8 is a diagram illustrating an electromotive force detected when an antenna attached to the body surface has received a magnetic field generated by the antenna illustrated in FIG. 6.

The following description assumes, as illustrated in FIG. 6, an orthogonal coordinate system $X_L Y_L Z_L$ where: the origin ($O_L$) is set at the gravity of the antenna 31, shaped into a circular loop, which is placed inside the capsule endoscope 3; and the $Z_L$-axis extends in the direction in which the normal line of a plane corresponding to the opening of the circular loop extends. In this case, the respective polar coordinate components of an electromagnetic field that is formed at any position P by a current flowing through the antenna 31 are expressed by the following expressions:

$$H_r = (IS/2\pi)(jk/r^2 + 1/r^3)\exp(-jkr)\cos\theta,$$

$$H_\theta = (IS/4\pi)(-k^2/r + jk/r^2 + 1/r^3)\exp(-jkr)\sin\theta, \text{ and}$$

$$E_\psi = -(j\omega\mu IS/4\pi)(jk/r + 1/r^2)\exp(-jkr)\sin\theta. \quad (1)$$

Here, $H_r$ and $H_\theta$ denote magnetic field components, and $E_\psi$ an electric field component. Further, I and S represent a current flowing through the antenna 31 and the area of the plane corresponding to the opening of the circular loop that constitutes the antenna 31, respectively. In addition, $k = \omega(\in\mu)^{1/2}$ ($\in$ is a dielectric constant, and $\mu$ a magnetic permeability) is a wavenumber, and j an imaginary unit. Here, in expressions (1), the $r^{-1}$ term represents a radiated electromagnetic field component, the $r^{-2}$ term an induced electromagnetic field component, and the $r^{-3}$ term a static magnetic field component.

When the electromagnetic field generated by the antenna 31 placed inside the capsule endoscope 3 has a high frequency, and, as illustrated in FIG. 1, the capsule endoscope 3 is located a sufficient distance away from each of the receiving antennas attached to the body surface of the subject 2, the radiated electromagnetic field component is the largest among all the components of an electromagnetic field (electromagnetic wave) that reaches the receiving antenna. Hence, the induced electromagnetic field and static magnetic field components are smaller than the radiated electromagnetic field component, and are found negligible. Therefore, expressions (1) are rewritten as expressions (2) below:

$$H_r = 0,$$

$$H_\theta = (IS/4\pi)(-k^2/r)\exp(-jkr)\sin\theta, \text{ and}$$

$$E_\psi = -(j\omega\mu IS/4\pi)(jk/r)\exp(-jkr)\sin\theta. \quad (2)$$

Given that each of the receiving antennas attached to the body surface of the subject 2 is an antenna provided for the purpose of detecting an electric field, an expression from expressions (2) that is needed for the detection is the electric field $E_\psi$. The electric field $E_\psi$ from expressions (2) represents a radiated electric field, and this is considered as a result from Alternating Current Theory. For this reason, the instantaneous value of the electric field $E_\psi$ is obtained by multiplying by $\exp(j\omega t)$ both sides of $E_\psi$, which is from expressions (2), and extracting the real part.

$$E_\psi \exp(j\omega t) = -(j\omega\mu IS/4\pi)(jk/r)\exp(-jkr)\sin\theta \exp(j\omega t) \quad (3)$$
$$= (\omega\mu ISk/4\pi r)(\cos U + j\sin U)\sin\theta,$$

where $U=\omega t - kr$. Here, when the real part of expression (3) is extracted, the instantaneous value $E'_\psi$ of the electric field $E_\psi$ is given as:

$$E'_\psi = (\omega\mu ISk/4\pi r)\cos U \sin\theta. \quad (4)$$

Further, when expression (4) is represented in the orthogonal coordinate system $X_L Y_L Z_L$, the components $E_{Lx}$, $E_{Ly}$, and $E_{Lz}$ are expressed as:

$$E_{Lx} = E'_\psi \sin\psi = (\omega\mu ISk/4\pi r^2)\cos U \cdot (-y_L),$$

$$E_{Ly} = E'_\psi \cos\psi = (\omega\mu ISk/4\pi r^2)\cos U \cdot x_L, \text{ and}$$

$$E_{Lz} = 0. \quad (5)$$

While being propagated through a medium, as illustrated in FIG. 7, energy of an electromagnetic wave is absorbed by the medium, through which the electromagnetic wave is propagated, in a manner dependent on characteristics (such as an electric conductivity) of the medium. The electromagnetic wave exponentially attenuates with an attenuation factor $\alpha_d$ as it is propagated, for example, in the x direction, and is expressible using expression (6) given below:

$$A_r = \exp(-\alpha_d x), \text{ and}$$

$$\alpha_d = (\omega^2 \in \mu/2)^{1/2}[(1+\kappa^2/(\omega^2 \in^2))^{1/2} - 1]^{1/2}, \quad (6)$$

where: $\in = \in_o \in_r$ ($\in_o$: an electric conductivity in vacuum, $\in_r$: a relative permittivity); $\mu = \mu_o \mu_r$ ($\mu_o$: a magnetic permeability in vacuum, $\mu_r$: a relative magnetic permeability); $\omega$ denotes an angular frequency; and $\kappa$ an electric conductivity.

Consequently, with attributes of the living body taken into consideration, the components $E_{Lx}$, $E_{Ly}$, and $E_{Lz}$ of the instantaneous value $E_L$ of the electric field in the orthogonal coordinate system $X_L Y_L Z_L$ are expressed as:

$$E_{Lx} = A_r E'_\psi \sin\psi = \exp(-\alpha_d x)(\omega\mu ISk/4\pi r^2)\cos U \cdot (-y_L)$$

$$E_{Ly} = A_r E'_\psi \cos\psi = \exp(-\alpha_d x)(\omega\mu ISk/4\pi r^2)\cos U \cdot x_L,$$
and $$E_{Lz} = 0. \quad (7)$$

Further, given below is a formula with which the position P in the orthogonal coordinate system $X_L Y_L Z_L$ having the origin set at the antenna 31 of the capsule endoscope 3 is transformed into one in the orthogonal coordinate system $X_w Y_w Z_w$ having the origin set at the center of gravity of the subject 2:

$$\begin{pmatrix} x_{LP} \\ y_{LP} \\ z_{LP} \end{pmatrix} = R^{-1}\left[\begin{pmatrix} x_{WP} \\ y_{WP} \\ z_{WP} \end{pmatrix} - \begin{pmatrix} x_{WG} \\ y_{WG} \\ z_{WG} \end{pmatrix}\right] = \begin{pmatrix} R_{00} & R_{01} & R_{02} \\ R_{10} & R_{11} & R_{12} \\ R_{20} & R_{21} & R_{22} \end{pmatrix}\left[\begin{pmatrix} x_{WP} \\ y_{WP} \\ z_{WP} \end{pmatrix} - \begin{pmatrix} x_{WG} \\ y_{WG} \\ z_{WG} \end{pmatrix}\right], \quad (8)$$

where $(x_{WP}, y_{WP}, z_{WP})$ and $(x_{WG}, y_{WG}, z_{WG})$ denote any position P and the position G of the antenna 31, respectively, when these positions are in the orthogonal coordinate system $X_w Y_w Z_w$. Additionally, R in the right side of expression (8) represents a rotation matrix for transformation between the orthogonal coordinate system $X_w Y_w Z_w$ and the orthogonal coordinate system $X_L Y_L Z_L$, and this is given by the following equation:

$$\begin{pmatrix} R_{00} & R_{10} & R_{20} \\ R_{01} & R_{11} & R_{21} \\ R_{02} & R_{12} & R_{22} \end{pmatrix} = \begin{pmatrix} \cos\alpha\cos\beta & -\sin\alpha & \cos\alpha\sin\beta \\ \sin\alpha\cos\beta & \cos\alpha & \sin\alpha\sin\beta \\ -\sin\beta & 0 & \cos\beta \end{pmatrix}, \quad (9)$$

where: $\alpha$ denotes a rotation angle about the Z-axis; and $\beta$ a rotation angle about the Y-axis.

Consequently, an electric field $E_w$ at any position P $(x_{WP}, y_{WP}, z_{WP})$ in the orthogonal coordinate system $X_w Y_w Z_w$ having the origin set at the center of gravity of the subject 2 is expressed as:

$$Ew = \begin{pmatrix} E_{Wx} \\ E_{Wy} \\ E_{Wz} \end{pmatrix} = R\begin{pmatrix} E_{Lx} \\ E_{Ly} \\ E_{Lz} \end{pmatrix} = \begin{pmatrix} R_{00} & R_{10} & R_{20} \\ R_{01} & R_{11} & R_{21} \\ R_{02} & R_{12} & R_{22} \end{pmatrix}\begin{pmatrix} E_{Lx} \\ E_{Ly} \\ E_{Lz} \end{pmatrix}. \quad (10)$$

Plugging expressions (7) to (9) into expression (10) provides expression (11) that gives the electric field $E_W$, which is expressed as:

$$\begin{pmatrix} E_{Wx} \\ E_{Wy} \\ E_{Wz} \end{pmatrix} = \quad (11)$$

$$\frac{k_1}{r^2}e^{-\alpha_d x}\begin{pmatrix} 0 & (z_{WP}-z_{WG}) & -(y_{WP}-y_{WG}) \\ (z_{WP}-z_{WG}) & 0 & (x_{WP}-x_{WG}) \\ (y_{WP}-y_{WG}) & -(x_{WP}-x_{WG}) & 0 \end{pmatrix}\begin{pmatrix} g_x \\ g_y \\ g_z \end{pmatrix},$$

where: $k_1$ is a constant; and a vector $(g_x, g_y, g_z)$ denotes the direction of the antenna 31.

Further, an electromotive force $V_1$ detected when the first receiving antenna 41 constituting the acquisition antenna 4 receives the electric field $E_W$ generated by the antenna 31 is calculable using a scalar product of the electric field $E_W$ and a vector $D_1 = (D_{x1}, D_{y1}, D_{z1})$ that represents the direction of the first receiving antenna 41 (the element section 41*a*) of the acquisition antenna 4 in the coordinate system with the origin set at the subject 2, with an expression given as:

$$V_1 = k_2(E_{Wx}D_{x1} + E_{Wy}D_{y1} + E_{Wz}D_{z1}), \quad (12)$$

where $k_2$ is a constant. The same calculation makes it also possible to obtain, with respect to the respective multiple receiving antennas of the acquisition antenna 4 that are placed on the body of the subject 2, electromotive forces $V_2$ to $V_8$ detected when the second to eighth receiving antennas 42 to 48 receive the electric field $E_W$.

Here, the position and the direction of the antenna 31 are obtained through iterative refinement (using the Gauss-Newton method). Hereinafter, a vector $x=(x_{WG}, y_{WG}, z_{WG}, g_x, g_y, g_z)$ is defined, which takes as parameters the position ($x_{WG}, y_{WG}, z_{WG}$) and the direction ($g_x, g_y, g_z$) of the antenna 31 in the coordinate system $X_W Y_W Z_W$. Further, the vector having both of the parameters at initial values is set as $x^{(0)}$.

From now on, a process to be performed upon completion of the process for obtaining an f-th order estimated value $x^{(f)}$ (f=0, 1, and so on) through iterative refinement is described. In this process, the Taylor expansion about $x^{(f)}$ is applied to a model function $V(x)$ in which the electromotive forces $V_1(x)$, $V_2(x)$, ..., and $V_8(x)$ generated at the first to eighth receiving antennas 41 to 48 are taken as elements. This provides a first-order approximation expressed as:

$$V(x) = V(x^{(f)}) + \left[\frac{\partial V(x)}{\partial x}\right]_{x=x^{(f)}} (x - x^{(f)}) \quad (13)$$

Here, when $Vm^{(f)}$ is defined as electromotive forces measured by the receiving antennas, the observation equation thereof is expressed as:

$$Vm^{(f)} \cong V(x^{(f)}) + \left[\frac{\partial V(x)}{\partial x}\right]_{x=x^{(f)}} (x - x^{(f)}) (\text{error } \sigma) \quad (14)$$

Here, the near equality sign includes an error $\sigma$.

The first term in the right side of equation (14) is moved to the left side, and $$\Delta Vm^{(f)} = Vm^{(f)} - V(x^{(f)}), \quad (15)$$

$$\Delta x^{(f)} = x - x^{(f)}, \text{ and} \quad (16)$$

$$A_{hs}^{(f)} = \left(\frac{\partial V_s(x)}{\partial x_h}\right)_{x_h = x_h^{(f)}} \quad (17)$$

(h = 1 to 6, s = 1 to 8, $(x_1, x_2, x_3, x_4, x_5, x_6) = (x_{WG}, y_{WG}, z_{WG}, g_x, g_y, g_z)$)

are plugged into equation (14), whereby $$\Delta Vm^{(f)} \cong A^{(f)} \Delta x^{(f)} (\text{error } \sigma) \quad (18)$$

is provided. $\Delta x^{(f)}$, which is the solution of expression (18), provides the amounts of update, and is expressed as:

$$\Delta x^{(f)} = (A^{(f)t} W A^{(f)})^{-1} A^{(f)t} W \Delta Vm^{(f)}, \quad (19)$$

where: $A^{(f)}$ denotes a matrix taking expression (17) as elements; and $A^t$ the transposed matrix of A. In addition, W is a weighting matrix, which is expressed as:

$$W = \begin{bmatrix} \sigma_0^2 & 0 & 0 & \cdots & 0 \\ 0 & \sigma_1^2 & 0 & \cdots & 0 \\ 0 & 0 & \sigma_2^2 & \cdots & 0 \\ \vdots & \vdots & \vdots & \ddots & \cdots \\ 0 & 0 & 0 & \cdots & \sigma_7^2 \end{bmatrix}, \quad (20)$$

where $\sigma_i$ (i=0, 1, ..., and 7) of the weighting matrix W are amounts of change that occur to measured voltages on the receiving antennas, and are, for example, environment-related noise. Here, when the magnitude of the amounts of update $\Delta x^{(f)}$ is not larger than a predetermined threshold, the iterative refinement is ended, so that the elements of the estimated value $x^{(f)}$ are determined to be the position and the direction of the antenna 31.

On the other hand, when the magnitude of the amounts of update $\Delta x^{(f)}$ exceeds the predetermined threshold, the iterative refinement is continued with the order incremented by 1. At this time, the amounts of update $\Delta x^{(f+1)}$ are obtained in the same manner as described above, after the (f+1)-th order estimated value is obtained as:

$$x^{(f+1)} = x^{(f)} + \Delta x^{(f)}. \quad (21)$$

Figure 9:
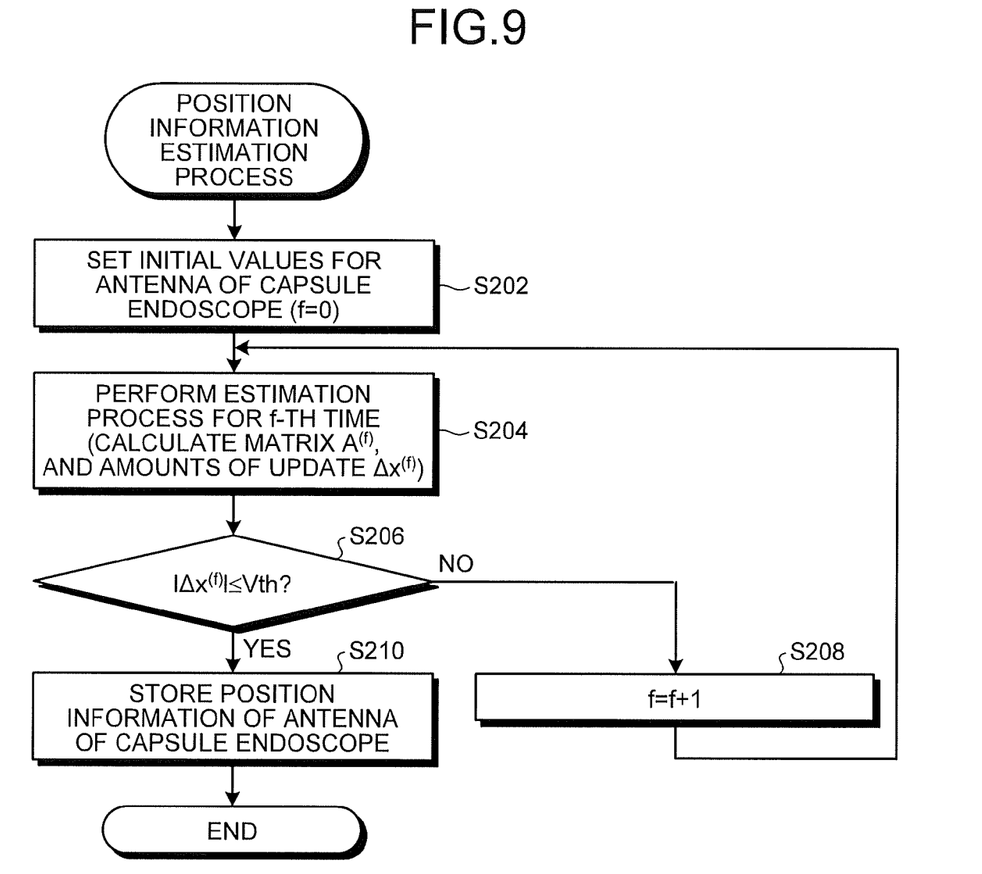
FIG. 9 is a flowchart illustrating a position information estimation process to be performed by the body-insertable apparatus system according to the first embodiment of the present invention.

Performing the estimation process as described above enables highly accurate estimation (calculation) of the position and the direction. In addition, the flow of the position information estimation process is set up as illustrated in FIG. 9. FIG. 9 is a flowchart illustrating the position information estimation process to be performed by the body-insertable apparatus system according to the first embodiment of the present invention.

First of all, the control unit 61 sets the initial values of the position and the direction of the antenna 31 (step S202). The control unit 61 additionally sets the parameter f to 0, where the parameter f denotes the estimation process performed for the f-th time when the estimation process for the position and the direction of the antenna 31 is performed. The control unit 61 also sets the frame number N for an image obtained by the capsule endoscope 3 to 1. Note that position information of the first to eighth receiving antennas 41 to 48 constituting the acquisition antenna 4 to be detachably attached to the body surface of the subject 2 is also stored in the storage unit 65 or the like beforehand. Then, the control unit 61 performs a process (the estimation process performed for the f-th time) for calculating the matrix $A^{(f)}$ and the amounts of update $\Delta x^{(f)}$ in the above described manner by using the electromotive force $Vm^{(f)}$ that corresponds to the first image frame obtained by the antennas (step S204).

Then, the control unit 61 determines whether, for example, the magnitude $|\Delta x^{(f)}|$ of the amounts of update $\Delta x^{(f)}$ is smaller than or equal to a predetermined value Vth (step S206). Then, when the magnitude $|\Delta x^{(f)}|$ of the amounts of update $\Delta x^{(f)}$ is larger than a predetermined value Vth (S206: No), the flow proceeds to step S208, where the control unit 61 increments the parameter f by one. Then, the flow returns to step S204, and the control unit 61 repeats the estimation process until the condition in step S206 is satisfied. When the magnitude $|\Delta x^{(f)}|$ of the amounts of update $\Delta x^{(f)}$ that satisfies the condition in step S206 is obtained (S206: Yes), the control unit 61 stores position information on the position and the direction of the antenna 31 (referred to as position information of the antenna, in short, in the drawings) for the parameter f in the storage unit 65 while associating the information with the frame number N (step S210). Note that, as the value Vth to be used for the determination, different values may be provided for the position and the direction.

Further, the capsule endoscope 3 may be configured to store not only the frame number N but also data representing a time at which an image has been captured, and transmit the data representing the time also. The information processor 6 may also store, in the memory, data representing a time at which signals have been actually received thereby. In a case where the time at which an image is captured is almost the same as the time at which a corresponding signal has been actually received, only any one of these times may be stored. The information on such times may be utilized in detection of an approximate (local) moving speed of the capsule endoscope 3. Thereafter, the control unit 61 sets the initial values of the position and the direction of the antenna 31 to the position information on the position and the direction of the antenna 31 that has been obtained in step S208. Thereafter, the flow returns to step S204, where the control unit 61 performs the position information estimation process on the image, corresponding to the frame number N, that the determination unit 63 has determined to perform the position information estimation process on.

When the above described process is repeated, position information on the position and the direction of the antenna 31 is stored in the storage unit 65 of the information processor 6 sequentially (in a temporal sequence) together with pieces of image data captured by the capsule endoscope 3 and with the frame numbers N of the respective pieces of data. Estimation (calculation) of a movement locus taken by the antenna 31 inside the living body is enabled with the sequentially stored positions of the antenna 31. Since it is allowed to assume these positions of the antenna 31 to be the positions of the capsule endoscope 3, information necessary for estimating the movement locus taken by the capsule endoscope 3 inside the living body is stored in the storage unit 65. Consequently, with the information processor 6 connected to the cradle 6a as illustrated in FIG. 1, it is possible to display the image data, the frame numbers N, and the position information on the positions and directions of the antenna 31, which have been stored in the storage unit 65 of this information processor 6.

Figure 10:
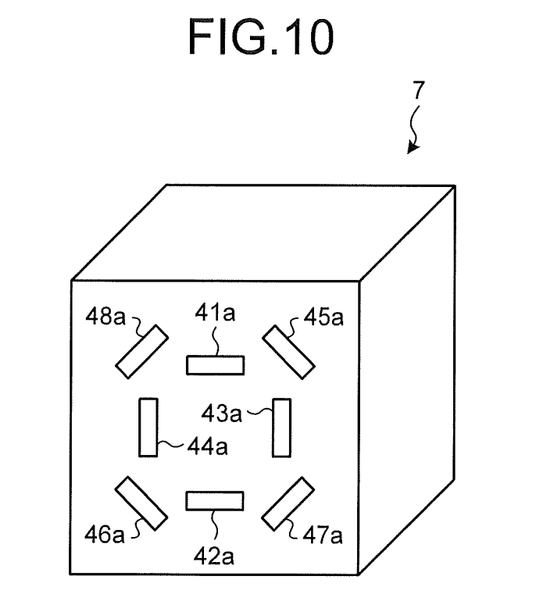
FIG. 10 is a diagram explaining the position information estimation process to be performed by the body-insertable apparatus system according to the first embodiment of the present invention.
Figure 11:
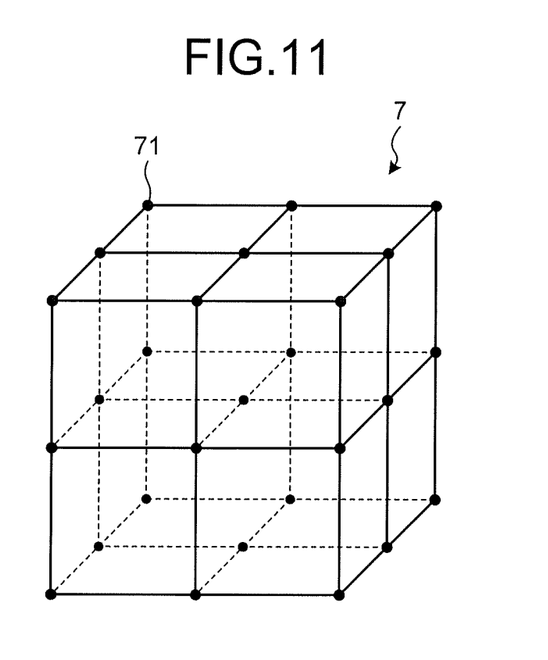
FIG. 11 is another diagram explaining the position information estimation process to be performed by the body-insertable apparatus system according to the first embodiment of the present invention.

Further, as illustrated in FIG. 10, a space 7 in which the capsule endoscope 3 is allowed to exist is set up beforehand with respect to the element sections 41a to 48a of the respective receiving antennas of the acquisition antenna 4 for the process, according to this first embodiment, for estimating the position information of the capsule endoscope 3. As illustrated in FIG. 11, in this space 7, eight spaces are obtained by equally dividing the space 7, and the vertexes of the respective spaces thus obtained are set beforehand as the start positions 71 (the positions plugged in as initial values) from which to start the estimation process. That is, in the case illustrated in FIG. 11, there are the start positions 71 set at 27 different locations. Further, one direction along any one of the X-, Y- and Z-axes is determined beforehand as a direction to be taken at the start at each one of the start positions 71, so that the estimation process is performed with respect to three patterns independent of each other (the X-, Y- and Z-axes) with respect to each one of the start positions 71. Therefore, the position information is estimated with the estimation process performed 81 times on one piece of image data (one frame number) acquired by the capsule endoscope 3.

According to the above described first embodiment, when the respective difference values between the signal levels corresponding to an acquired image at the respective receiving antennas and the signal levels acquired the previous time are smaller than the predetermined threshold, the process for estimating (deriving) the position information of the capsule endoscope 3 is not performed, and, instead, the position information of the capsule endoscope 3 that has been estimated the previous time is used as the position information of the capsule endoscope 3 that corresponds to the image acquired this time. This makes it possible to efficiently curtail the process for deriving the position information, and reduce the time required for deriving the position information.

Note that, although the above descried determination process as to the necessity to perform the position estimation is described on the assumption that the determination unit 63 determines whether at least any one of the difference values exceeds a threshold, that two or more of the difference values are larger than a threshold may be used as the condition for determining that the difference values exceed the threshold. Otherwise, the result of comparison between the largest one of the difference values and a threshold may be used as the condition for the determination.

Further, the signal levels acquired the previous time to be used in step S104 in FIG. 5 may be those corresponding to a frame that is one frame earlier than the current one, or may be those corresponding to a frame that is two or more frames earlier, such as those corresponding to a frame that is two frames earlier, than the current one.

Further, with regard to the above described space in which the capsule endoscope 3 is allowed to exist, the description assumes that the space is equally divided into eight spaces. However, that space may be equally divided into 16 spaces, or may be equally divided into 12 spaces (each having a vertical to horizontal ratio at 2 to 3).

The above described first embodiment is described on the assumption that the information processor 6 performs the above described processes such as the calculation of the difference values and the determination of the necessity to perform the estimation process. However, the receiving device 5 may be configured to perform these processes, alternatively.

Second Embodiment

Figure 12:
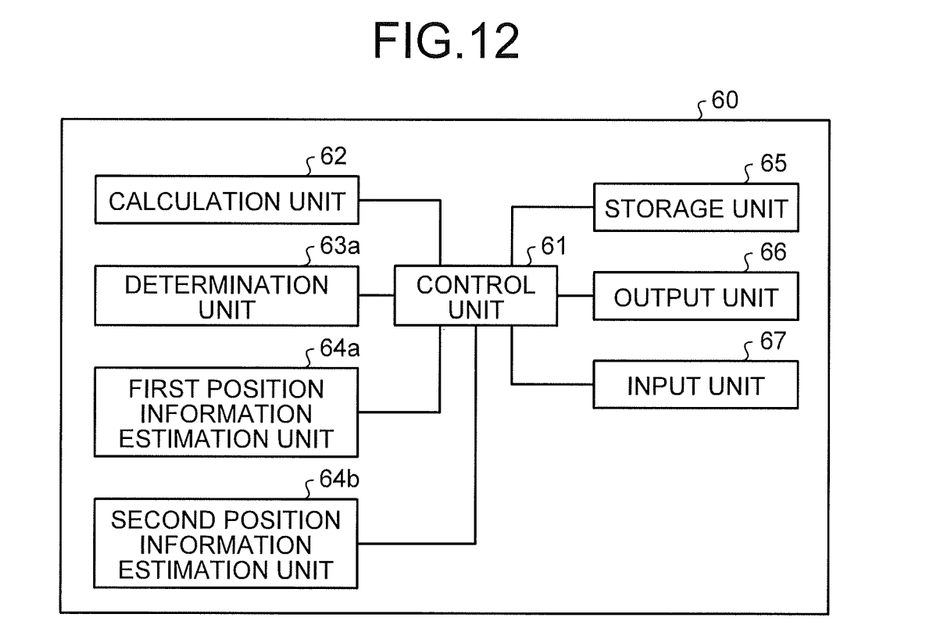
FIG. 12 is a block diagram illustrating the configuration of an information processor of a body-insertable apparatus system according to a second embodiment of the present invention.
Figure 13:
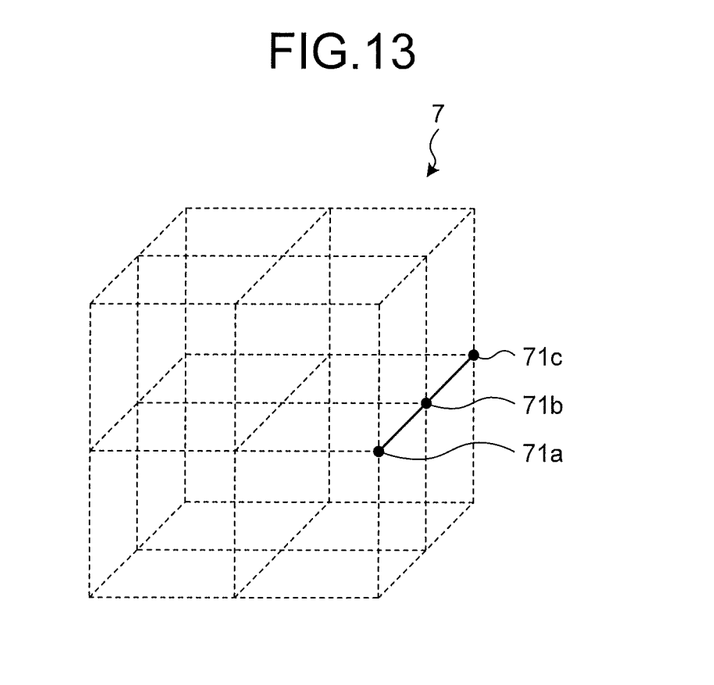
FIG. 13 is a diagram explaining a position information estimation process to be performed by the body-insertable apparatus system according to the second embodiment of the present invention.

FIG. 12 is a block diagram illustrating the configuration of an information processor of a body-insertable apparatus system according to a second embodiment of the present invention. FIG. 13 is a diagram explaining a position information estimation process in the body-insertable apparatus system according to the second embodiment of the present invention. Note that the same reference singes are used to designate the same constituent elements as those included in the information processor 6 described above using FIG. 2 and some other drawings.

An information processor 60 according to this second embodiment includes the control unit 61, the calculation unit 62, the storage unit 65, the output unit 66 and the input unit 67, which are all described above, and further includes: a determination unit 63a; a first position information estimation unit 64a that serves as position information estimation means; and a second position information estimation unit 64b that serves as simplified position information estimation means. The determination unit 63a refers to a first threshold and a second threshold (larger than the first threshold), which have been stored in the storage unit 65, to perform comparison of these thresholds with each of the difference values and thereby determine the necessity to perform the position information estimation process.

The first position information estimation unit 64a and the second position information estimation unit 64b estimate the position of the capsule endoscope 3 by deriving the position information of the capsule endoscope 3 in accordance with the predetermined thresholds. In this second embodiment, the first position information estimation unit 64a performs a process for estimating the position information at the 27 start positions (the directions along the X-, Y- and Z-axis are taken as start directions with respect to each of the locations) as in the case of the above described position information estimation process (see FIG. 11). Further, the second position information estimation unit 64b performs a process for estimating the position information at certain specific locations 71a, 71b, and 71c (three locations) in the space 7 as illustrated in FIG. 13.

The second position information estimation unit 64b categorizes the receiving antennas into one group of receiving antennas that have received relatively high signal levels, and the other group of receiving antennas that have received relatively low signal levels. Then, the second position information estimation unit 64b selects the receiving antenna that has received the highest signal level from the group of receiving antennas that have received relatively high signal levels. Then, the second position information estimation unit 64b sets, as the specific locations, the start positions that are close to the selected receiving antenna. For example, the second position information estimation unit 64b sets as the specific location 71a one of the start positions that is close to the selected receiving antenna. Further, the second position information estimation unit 64b performs a process for estimating the position information after selecting, as the specific locations (71b and 71c three locations), locations that are located backward of the specific location 71a in the space 7 as viewed from the receiving antennas.

Figure 14:
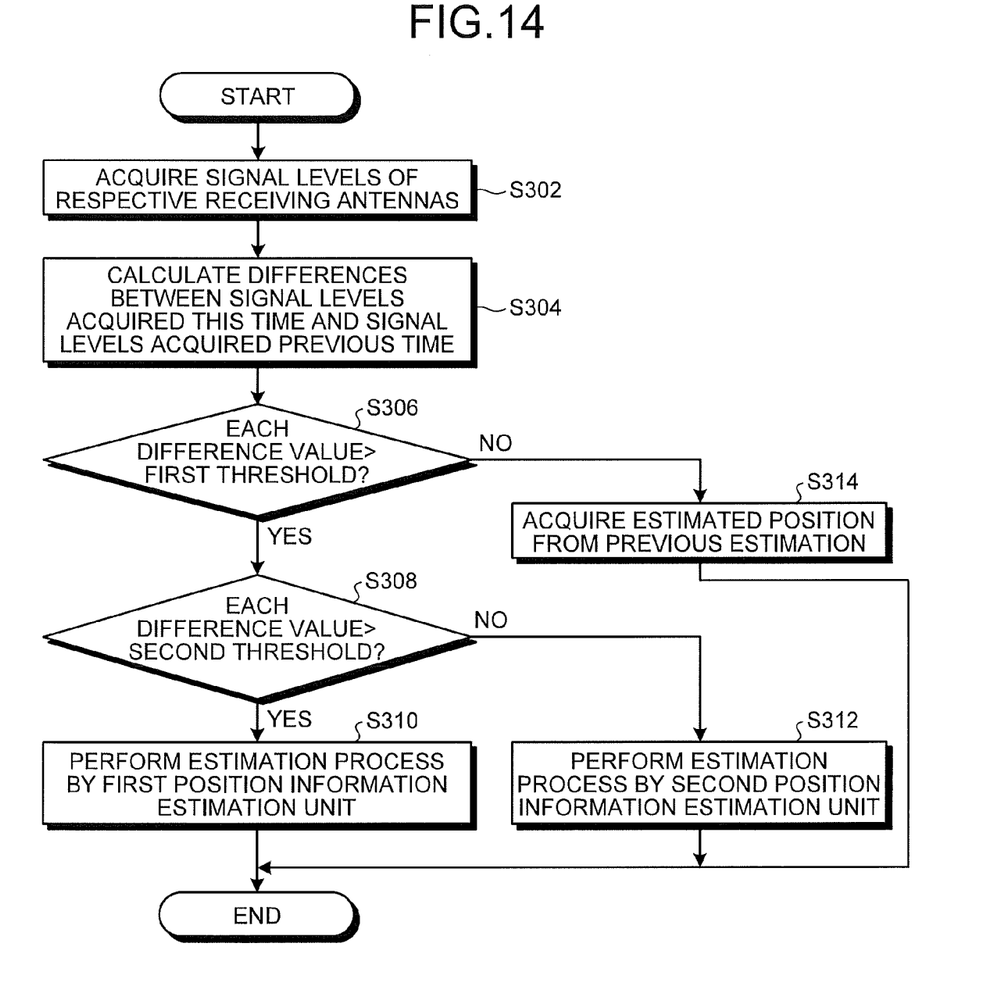
FIG. 14 is a flowchart illustrating a determination process, in the body-insertable apparatus system according to the second embodiment of the present invention, as to the necessity to perform position estimation.

Next, a determination process according to this second embodiment as to whether to estimate the position information is described with reference to FIG. 14. FIG. 14 is a flowchart illustrating the determination process, in the body-insertable apparatus system according to the second embodiment of the present invention, as to the necessity to perform position estimation. First of all, the control unit 61 acquires the respective signal levels acquired by the first to eighth receiving antennas 41 to 48 (step S302), and then, the calculation unit 62 calculates the absolute values (the respective difference values) of the respective differences between the signal levels at the first to eighth receiving antennas 41 to 48 acquired the previous time and the signal levels at the first to eighth receiving antennas 41 to 48 acquired this time (step S304).

The determination unit 63a compares each of the calculated difference values with the predetermined first threshold (step S306). Here, upon determining that at least any one of the difference values exceeds the first threshold (step S306: Yes), the determination unit 63a compares each of the difference values with the second threshold (step S308). When the determination unit 63a has determined that at least any one of the difference values exceeds the second threshold (step S308: Yes), the first position information estimation unit 64a performs the process for estimating the position information of the capsule endoscope 3 (step S310).

On the other hand, when the determination unit 63a has determined that all of the difference values are smaller than or equal to the second threshold (step S308: No), the second position information estimation unit 64b performs the process for estimating the position information of the capsule endoscope 3 (step S312). When the difference values are smaller than or equal to the second threshold, it is allowed to determine that the capsule endoscope 3 has moved to a position that necessitates the position estimation, but has moved only a relatively short distance. Therefore, the position information estimation process is performed with start positions, such as the specific locations 71a to 71c in FIG. 13, set based on the estimated position obtained the previous time. This makes it possible to further reduce the time required for the estimation process.

On the other hand, when the determination unit 63a has determined that all of the difference values are smaller than or equal to the first threshold (step S306: No), the control unit 61 acquires the estimated position estimated the previous time, and associates the corresponding image data and this estimated position with each other. At this time, the control unit 61 acquires the estimated position obtained the previous time because, when the difference values are smaller than or equal to the first threshold, it is allowed to determine that the capsule endoscope 3 has not moved a distance long enough to make it necessary to perform the position estimation again (step S314).

According to the above described second embodiment, when the respective difference values between the signal levels, corresponding to the acquired image, at the respective receiving antennas and the signal levels acquired the previous time are smaller than the predetermined threshold, the process for estimating (deriving) the position information of the capsule endoscope 3 is not performed, and, instead, the position information of the capsule endoscope 3 that has been estimated the previous time is used as the position information of the capsule endoscope 3 that corresponds to the image acquired this time, as in the case of the first embodiment. This makes it possible to efficiently curtail the process for deriving the position information, and reduce the time required for deriving the position information. In addition, the estimation process simplified in a manner dependent on the amounts of change in signal levels enables further reduction of the time required for the estimation process.

Here, the second position information estimation unit 64b may perform the estimation process after selecting, with respect to the start position that is the closest to a position estimated the previous time, which may be the specific location 71b for example, the start positions (the specific directions 71a and 71c) that are next thereto and that are in predetermined directions therefrom. Further, the second position information estimation unit 64b is described as being configured to select as the specific locations the three locations as indicated in FIG. 13. However, the second position information estimation unit 64b may be configured to select any number of the specific locations in the space 7 illustrated in FIG. 11 as long as the number is smaller than or equal to 26.

Note that, in the above described second embodiment, the first position information estimation unit 64a or the second position information estimation unit 64b may perform the position information estimation process based on the magnitude relationships of the respective difference values with one threshold.

Further, in the first and second embodiments, the receiving device may be configured to have the function of the position information estimation and display the position of the capsule endoscope in real time on a display unit provided to the receiving device.

As described heretofore, the position information estimation system according to the present invention is useful in reducing the time required for deriving the position information of a capsule endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A position information estimation system comprising:
a body-insertable apparatus that is inserted into a subject and moves through an inside of the subject;
a receiving unit that receives information from the body-insertable apparatus; and
an information processor that performs processes on the information acquired from the receiving unit,
wherein the receiving unit includes an acquisition antenna that includes a plurality of receiving antennas and acquires the information from the body-insertable apparatus, and
the receiving unit or the information processor includes:
a calculation unit that calculates difference values between signal levels acquired from the plurality of receiving antennas and corresponding signal levels previously acquired from the plurality of receiving antennas;
a determination unit that compares each of the difference values and a threshold and determines whether to estimate position information; and
a position information estimation unit that, when the determination unit has determined that it is necessary to estimate the position information, estimates position information of the body-insertable apparatus.

2. The position information estimation system according to claim 1, further comprising a simplified position information estimation unit that performs simplified estimation which is a simplified form of the estimation performed by the position information estimation unit,
wherein the determination unit determines, by using a first threshold, the necessity to perform estimation, and determines, by using a second threshold, which of the position information estimation unit and the simplified position information estimation unit is to perform estimation as the estimation of the position information of the body-insertable apparatus, the second threshold being larger than the first threshold.

3. The position information estimation system according to claim 1, wherein the acquisition antenna includes the plurality of receiving antennas of which positional relationship is fixed on one sheet.

4. The position information estimation system according to claim 3, wherein the plurality of receiving antennas includes:
a first receiving antenna and a second receiving antenna placed at positions on a plane that are the same distance away from a reference point and that are opposed to each other across the reference point;
a third receiving antenna and a fourth receiving antenna placed at positions that are located 90 degrees around the reference point from the first receiving antenna and the second receiving antenna, respectively, on the plane;
a fifth receiving antenna and a sixth receiving antenna placed at positions that are, on the plane, closer to the outer circumference than the first receiving antenna and the second receiving antenna are, and that are located 45 degrees around the reference point from the first receiving antenna and the second receiving antenna, respectively on the plane; and
a seventh receiving antenna and an eighth receiving antenna placed at positions that are located 90 degrees around the reference point from the fifth receiving antenna and the sixth receiving antenna, respectively, on the plane.

5. The position information estimation system according to claim 1, wherein the position information estimation unit estimates the position information by using signals acquired from the plurality of receiving antennas.

6. The position information estimation system according to claim 1, wherein:
the calculation unit acquires the signal levels from the plurality of receiving antennas, and calculates the difference values between the acquired signal levels and the previously acquired corresponding signal levels for each of the plurality of receiving antennas, and
the determination unit compares each of the difference values and the threshold and determines to use previously estimated position information instead of estimating position information when all the difference values are smaller than the threshold.

7. The position information estimation system according to claim 3, wherein the plurality of receiving antennas includes:
a first group of receiving antennas placed at positions on a plane that are a same distance away from a reference point; and
a second group of receiving antennas placed at positions that are, on the plane, closer to the outer circumference than the first group of receiving antennas.

* * * * *